United States Patent
Lee

(10) Patent No.: US 9,034,255 B2
(45) Date of Patent: May 19, 2015

(54) PURIFIED HYDROGEN PEROXIDE GAS MICROBIAL CONTROL METHODS AND DEVICES

(71) Applicant: Lee Antimicrobial Solutions LLC, Stamford, CT (US)

(72) Inventor: James D. Lee, Stamford, CT (US)

(73) Assignee: Lee Antimicrobial Solutions LLC, Stamford, CT (US)

( * ) Notice: Subject to any disclaimer, the term of this patent is extended or adjusted under 35 U.S.C. 154(b) by 0 days.

(21) Appl. No.: 14/175,551

(22) Filed: Feb. 7, 2014

(65) Prior Publication Data

US 2014/0154133 A1  Jun. 5, 2014

Related U.S. Application Data

(60) Continuation of application No. 13/425,736, filed on Mar. 21, 2012, now Pat. No. 8,685,329, which is a division of application No. 12/187,755, filed on Aug. 7, 2008, now Pat. No. 8,168,122.

(60) Provisional application No. 61/031,580, filed on Feb. 26, 2008, provisional application No. 60/954,566, filed on Aug. 7, 2007.

(51) Int. Cl.
*A61L 2/20* (2006.01)
*A61L 9/20* (2006.01)

(52) U.S. Cl.
CPC .................. *A61L 2/208* (2013.01); *A61L 9/205* (2013.01); *A61L 2209/211* (2013.01)

(58) Field of Classification Search
CPC ........................................ A61L 2/208
USPC ................. 422/4, 28, 34, 120, 121, 186.3
See application file for complete search history.

(56) References Cited

U.S. PATENT DOCUMENTS

| 5,667,753 A | 9/1997 | Jacobs et al. |
| 5,674,450 A | 10/1997 | Lin et al. |
| 5,785,934 A | 7/1998 | Jacobs et al. |
| 5,876,666 A | 3/1999 | Lin et al. |
| 5,948,355 A | 9/1999 | Fujishima et al. |

(Continued)

FOREIGN PATENT DOCUMENTS

| EP | 0 306 301 A1 | 3/1989 |
| EP | 0 452 780 A2 | 4/1991 |

(Continued)

OTHER PUBLICATIONS

Block, "Disinfection, sterilization, and preservation," *Peroxygen Compounds*, 187-191 (2001).

(Continued)

*Primary Examiner* — Sean E Conley
(74) *Attorney, Agent, or Firm* — Arnold & Porter LLP

(57) ABSTRACT

The present invention relates to methods and devices for providing microbial control and/or disinfection/remediation of an environment. The methods generally comprise: generating a Purified Hydrogen Peroxide Gas (PHPG) that is substantially free of, e.g., hydration, ozone, plasma species, and/or organic species; and directing the gas comprising primarily PHPG into the environment such that the PHPG acts to provide microbial control and/or disinfection/remediation in the environment, preferably both on surfaces and in the air.

22 Claims, 2 Drawing Sheets

SECTION A-A

(56) References Cited

U.S. PATENT DOCUMENTS

| | | |
|---|---|---|
| 6,500,387 B1 | 12/2002 | Bigelow |
| 7,132,083 B2 | 11/2006 | Martin |
| 7,914,733 B2 | 3/2011 | Carey |
| 2005/0175500 A1 | 8/2005 | Adams et al. |
| 2005/0186124 A1 | 8/2005 | Fink et al. |
| 2005/0191205 A1 | 9/2005 | Uslenghi et al. |
| 2005/0255172 A1 | 11/2005 | Omidbakhsh |
| 2009/0246091 A1 | 10/2009 | Vanderspurt et al. |

FOREIGN PATENT DOCUMENTS

| | | | |
|---|---|---|---|
| EP | 0 978 690 A1 | | 9/2000 |
| EP | 0 978 690 A2 | | 9/2000 |
| EP | 1 491 218 A1 | | 12/2004 |
| JP | 1-267131 | | 10/1989 |
| JP | U3068844 | | 5/2000 |
| JP | 2001-170144 | | 6/2001 |
| JP | 2006-233216 | | 9/2006 |
| JP | 2010-535807 | | 11/2010 |
| WO | 97/09073 | | 3/1997 |
| WO | 01/78793 | A1 | 10/2001 |
| WO | 2004/112958 | A1 | 12/2004 |
| WO | 2006/111088 | A1 | 10/2006 |
| WO | 2009/021108 | A1 | 2/2009 |
| WO | 2010/093796 | A1 | 8/2010 |

OTHER PUBLICATIONS

International Search Report for PCT/US2008/072454 dated Nov. 28, 2008.

Written Opinion and Search Report mailed on Apr. 11, 2012, in Singapore Patent Application No. 201000787-0.

PURIFIED HYDROGEN PEROXIDE GAS MICROBIAL CONTROL METHODS AND DEVICES

CROSS REFERENCE TO RELATED APPLICATIONS

This application is a continuation application of U.S. application Ser. No. 13/425,736, filed Mar. 21, 2012 (now U.S. Pat. No. 8,685,329, issued Apr. 1, 2014), which is a divisional application of U.S. application Ser. No. 12/187,755, filed Aug. 7, 2008 (now U.S. Pat. No. 8,168,122, issued May 1, 2012), which claims priority to U.S. Provisional Application No. 60/954,566, filed Aug. 7, 2007, and U.S. Provisional Application No. 61/031,580, filed Feb. 26, 2008, each of which is hereby incorporated by reference in their entireties.

FIELD OF INVENTION

The present invention generally relates to infection and microbial control methodologies and devices related thereto.

BACKGROUND OF INVENTION

Pathogenic microbes, molds, mildew, spores, and organic and inorganic pollutants are commonly found in the environment. Microbial control and disinfection in environmental spaces is desirable to improve health. Numerous ways have been used to in the past in an attempt to purify air and disinfect surfaces. For example, it is already known that Reactive Oxidizing Species (ROS) produced by, e.g., photocatalytic oxidation process can oxidize organic pollutants and kill microorganisms. More particularly, hydroxyl radical, hydroperoxyl radicals, chlorine and ozone, end products of the photocatalytic reaction, have been known to be capable of oxidizing organic compounds and killing microorganisms. However, there are limitations to the known methods and devices, not only due to efficacy limitation but also due to safety issues.

ROS is the term used to describe the highly activated air that results from exposure of ambient humid air to ultraviolet light. Light in the ultraviolet range emits photons at a frequency that when absorbed has sufficient energy to break chemical bonds. UV light at wavelengths of 250-255 nm is routinely used as a biocide. Light below about 181 nm, up to 182-187 nm is competitive with corona discharge in its ability to produce ozone. Ozonation and UV radiation are both being used for disinfection in community water systems. Ozone is currently being used to treat industrial wastewater and cooling towers.

Hydrogen peroxide is generally known to have antimicrobial properties and has been used in aqueous solution for disinfection and microbial control. Attempts to use hydrogen peroxide in the gas phase, however, have previously been hampered by technical hurdles to the production of Purified Hydrogen Peroxide Gas (PHPG). Vaporized aqueous solutions of hydrogen peroxide produce an aerosol of microdroplets composed of aqueous hydrogen peroxide solution. Various processes for "drying" vaporized hydrogen peroxide solutions produce, at best, a hydrated form of hydrogen peroxide. These hydrated hydrogen peroxide molecules are surrounded by water molecules bonded by electrostatic attraction and London Forces. Thus, the ability of the hydrogen peroxide molecules to directly interact with the environment by electrostatic means is greatly attenuated by the bonded molecular water, which effectively alters the fundamental electrostatic configuration of the encapsulated hydrogen peroxide molecule. Further, the lowest concentration of vaporized hydrogen peroxide that can be achieved is generally well above the 1.0 ppm OSHA workplace safety limit, making these processes unsuitable for use in occupied areas.

Photocatalysts that have been demonstrated for the destruction of organic pollutants in fluid include but are not limited to $TiO_2$, $ZnO$, $SnO_2$, $WO_3$, $CdS$, $ZrO_2$, $SB_2O_4$ and $Fe_2O_3$. Titanium dioxide is chemically stable, has a suitable bandgap for UV/Visible photoactivation, and is relatively inexpensive. Therefore, photocatalytic chemistry of titanium dioxide has been extensively studied over the last thirty years for removal of organic and inorganic compounds from contaminated air and water.

Because photocatalysts can generate hydroxyl radicals from adsorbed water when activated by ultraviolet light of sufficient energy, they show promise for use in the production of PHPG for release into the environment when applied in the gas phase. Existing applications of photocatalysis, however, have focused on the generation of a plasma containing many different reactive chemical species. Further, the majority of the chemical species in the photocatalytic plasma are reactive with hydrogen peroxide, and inhibit the production of hydrogen peroxide gas by means of reactions that destroy hydrogen peroxide. Also, any organic gases that are introduced into the plasma inhibit hydrogen peroxide production both by direct reaction with hydrogen peroxide and by the reaction of their oxidized products with hydrogen peroxide.

The photocatalytic reactor itself also limits the production of PHPG for release into the environment. Because hydrogen peroxide has greater chemical potential than oxygen to be reduced as a sacrificial oxidant, it is preferentially reduced as it moves downstream in photocatalytic reactors as rapidly as it is produced by the oxidation of water.

Oxidation $$2\text{photons}+2H_2O\rightarrow 2OH^*+2H^++2e^-$$

$$2OH^*\rightarrow H_2O_2$$

Reduction $$H_2O_2+2H^++2e^-\rightarrow 2H_2O$$

Additionally, several side reactions generate a variety of species that become part of the photocatalytic plasma, and which inhibit the production of PHPG for release into the environment as noted above.

The wavelengths of light used to activate photocatalysts are also energetic enough to photolyze the peroxide bond in a hydrogen peroxide molecule and are also an inhibitor in the production of PHPG for release into the environment. Further, the practice of using wavelengths of light that produce ozone introduces yet another species into the photocatalytic plasma that destroys hydrogen peroxide.

$$O_3+H_2O_2\rightarrow H_2O+2O_2$$

In practice, photocatalytic applications have focused on the production of a plasma, often containing ozone, used to oxidize organic contaminants and microbes. Such plasmas are primarily effective within the confines of the reactor itself, by nature have limited chemical stability beyond the confines of the reactor, and actively degrade the limited amounts of hydrogen peroxide gas that they may contain. Further, because the plasma is primarily effective within the reactor itself, many designs maximize residence time to facilitate more complete oxidation of organic contaminants and microbes as they pass through the reactor. Since hydrogen peroxide has such a high potential to be reduced, the maximized residence time results in minimized hydrogen peroxide output.

Also, most applications of photocatalysis produce environmentally objectionable chemical species. First among these is ozone itself, an intentional product of many systems. Further, since organic contaminants that pass through a reactor are seldom oxidized in one exposure, multiple air exchanges are necessary to achieve full oxidation to carbon dioxide and water. As incomplete oxidation occurs, a mixture of aldehydes, alcohols, carboxylic acids, ketones, and other partially oxidized organic species is produced by the reactor. Often, photocatalytic reactors can actually increase the overall concentration of organic contaminants in the air by fractioning large organic molecules into multiple small organic molecules such as formaldehyde.

In summary, the production of PHPG for release into the environment is not achieved in the prior art. Methods of vaporizing aqueous hydrogen peroxide solutions produce, at best, hydrated forms of hydrogen peroxide. Also, though photocatalytic systems are capable of producing hydrogen peroxide, they have multiple limitations that severely inhibit PHPG production for release into the environment.

SUMMARY OF THE INVENTION

In one aspect of the invention, a method of providing microbial control and/or disinfection/remediation of an environment is disclosed. The method generally comprises (a) providing a photocatalytic cell that preferentially produces hydrogen peroxide gas; (b) generating a Purified Hydrogen Peroxide Gas (PHPG) that is substantially free of, e.g., hydration, ozone, plasma species, and/or organic species; and (c) directing the gas comprising primarily PHPG into the environment such that the PHPG acts to provide microbial control and/or disinfection/remediation in the environment, preferably both on surfaces and in the air.

In certain embodiments, the method comprises (a) exposing a metal, or metal oxide, catalyst to ultraviolet light in the presence of humid, purified ambient air under conditions so as to form Purified Hydrogen Peroxide Gas (PHPG) that is substantially free of, e.g., hydration, ozone, plasma species, and/or organic species; and (b) directing the PHPG into the environment such that the hydrogen peroxide gas acts to provide infection control and/or disinfection/remediation in the environment, preferably both on surfaces and in the air.

Another aspect of the invention relates to a diffuser apparatus for producing PHPG that is substantially free of, e.g., hydration, ozone, plasma species, and/or organic species. The diffuser apparatus generally comprises: (a) a source of ultraviolet light; (b) a metal oxide catalyst substrate structure; and (c) an air distribution mechanism.

Another aspect of the invention relates to the oxidation/removal of VOC's from ambient air by PHPG once it is released into the environment.

Another aspect of the invention relates to the removal of ozone from ambient air by PHPG once it is released into the environment.

These and other aspects of the invention will become apparent to those skilled in the art upon reading the present disclosure.

DETAILED DESCRIPTION OF THE PREFERRED EMBODIMENTS

Figure 1:
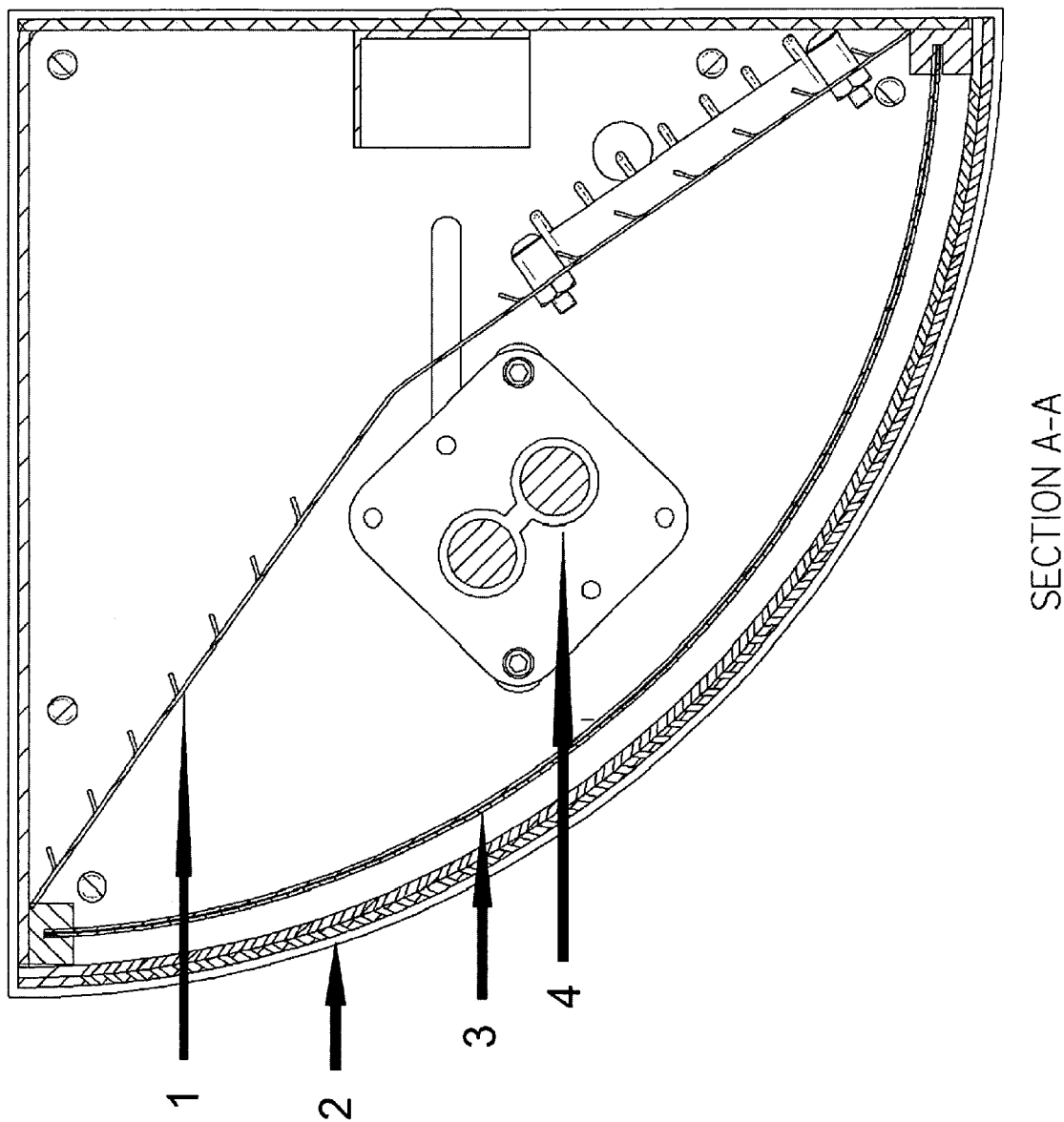
FIG. 1 is a cross-section of a particular embodiment of a diffuser apparatus of the present invention

The present invention relates generally to microbial control and/or disinfection/remediation methods and devices related thereto. In certain embodiments, photocatalytic processes may be utilized in the methods and devices described herein.

The fundamental nature of a photocatalytic process is to create active intermediates in a chemical reaction by absorption of light. This occurs when a photon of the appropriate wavelength strikes the photocatalyst. The energy of the photon is imparted to a valence band electron, promoting the electron to the conduction band, thus leaving a "hole" in the valence band. In the absence of an adsorbed chemical species, the promoted electron will decay and recombine with the valence band hole. Recombination is prevented when the valence band hole captures an electron from an oxidizable species—preferentially molecular water—adsorbed to an active surface site on the photocatalyst. Concurrently, a reducible species adsorbed on the catalyst surface—preferentially molecular oxygen—may capture a conduction band electron.

Upon initiation of the photocatalytic process, or at the entrance point of a photocatalytic reactor, the following reactions occur.

Oxidation

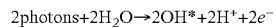

Reduction

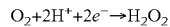

Once hydrogen peroxide has been produced, however, the photocatalyst preferentially reduces hydrogen peroxide instead of molecular oxygen, and the reaction shifts to the following equilibrium which takes place within the majority of the reactor volume.

Oxidation

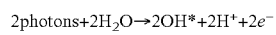

Reduction

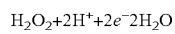

In the context of the present invention, Purified Hydrogen Peroxide Gas (PHPG) may be produced using a photocatalytic process with a purpose-designed morphology that enables the removal of hydrogen peroxide from the reactor before it is forced to undergo subsequent reduction by the photocatalyst. Denied ready availability of adsorbed hydrogen peroxide gas, the photocatalyst is then forced to preferentially reduce oxygen, rather than hydrogen peroxide. Hydrogen peroxide gas may then generally be produced simultaneously by both the oxidation of water and the reduction of dioxygen in the photocatalytic process. Without intending to be limited, in operation the amount of hydrogen peroxide produced may be doubled, then removed from the system before the vast majority of it can be reduced—thereby resulting in an output of PHPG that is up to 150 times greater than the incidental output of unpurified hydrogen peroxide from standard photocatalytic reactors under the same conditions. In the purpose-designed morphology the dominant reactions become:

Oxidation $$2\text{photons} + 2H_2O \rightarrow 2OH^* + 2H^+ + 2e^-$$

$$2OH^* \rightarrow H_2O_2$$

Reduction $$O_2 + 2H^+ + 2e^- \rightarrow H_2O_2$$

However, without being limited by theory, it should be noted that the microbial control and/or disinfection/remediation methods and devices of the invention are not achieved as a result of the photocatalytic process, but by the effects of PHPG once it is released into the environment.

Using morphology that permits immediate removal of hydrogen peroxide gas before it can be reduced, PHPG may be generated in any suitable manner known in the art, including but not limited to, any suitable process known in the art that simultaneously oxidizes water in gas form and reduces oxygen gas, including gas phase photo-catalysis, e.g., using a metal catalyst such as titanium dioxide, zirconium oxide, titanium dioxide doped with cocatalysts (such as copper, rhodium, silver, platinum, gold, etc.), or other suitable metal oxide photocatalysts. PHPG may also be produced by electrolytic processes using anodes and cathodes made from any suitable metal, or constructed from metal oxide ceramics using morphology that permits immediate removal of hydrogen peroxide gas before it can be reduced. Alternatively, PHPG may be produced by high frequency excitation of gaseous water and oxygen molecules on a suitable supporting substrate using morphology that permits immediate removal of hydrogen peroxide gas before it can be reduced.

In one aspect of the invention, a method of providing microbial control and/or disinfection/remediation of an environment is disclosed. The method generally comprises (a) generating a gas comprised of Purified Hydrogen Peroxide Gas (PHPG) that is substantially free of, e.g., hydration, ozone, plasma species, and/or organic species; and (b) directing the gas comprised of PHPG into the environment such that the PHPG acts to provide microbial control and/or disinfection/remediation in the environment, preferably both on surfaces and in the air.

In certain embodiments, the method comprises (a) exposing a metal, or metal oxide, catalyst to ultraviolet light in the presence of humid purified ambient air under conditions so as to form Purified Hydrogen Peroxide Gas (PHPG) that is substantially free of, e.g., hydration, ozone, plasma species, and/or organic species; and (b) directing the PHPG into the environment such that the PHPG acts to provide infection control and/or disinfection/remediation in the environment, preferably both on surfaces and in the air, removal of ozone from the ambient air, and removal of VOC's from the ambient air.

Figure 2:
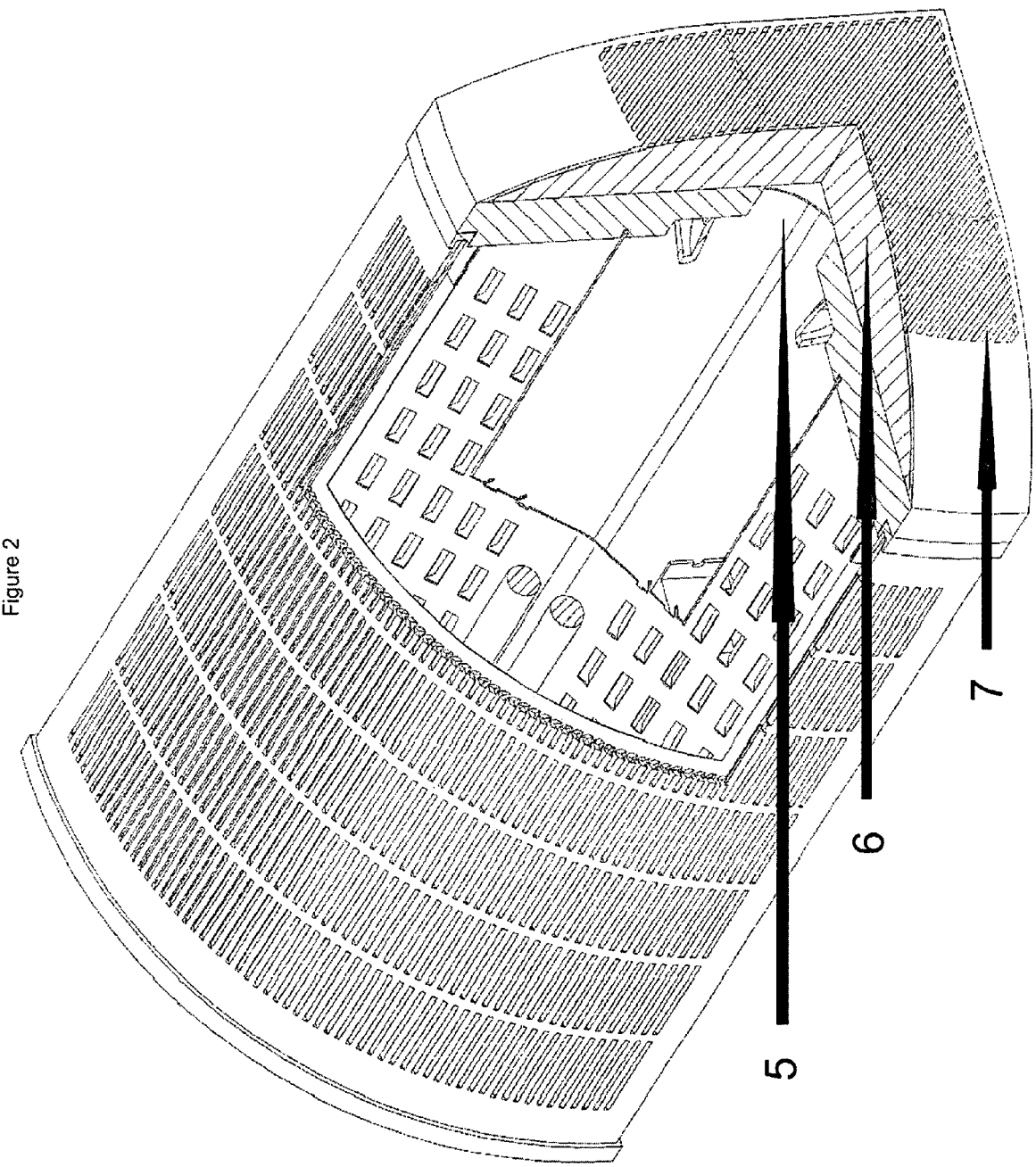
FIG. 2 is a cut away view of a particular embodiment of a diffuser apparatus of the present invention.

In one embodiment, the ultraviolet light produces at least one wavelength in a range above about 181 nm, above about 185 nm, above about 187 nm, between about 182 nm and about 254 nm, between about 187 nm and about 250 nm, between about 188 nm and about 249 nm, etc Another aspect of the invention relates to a diffuser apparatus for producing Purified Hydrogen Peroxide Gas (PHPG) that is substantially free of, e.g., hydration, ozone, plasma species, and/or organic species. With reference to FIGS. 1 and 2, the diffuser apparatus generally comprises: (a) a source of ultraviolet light 4; (b) a metal or metal oxide catalyst substrate structure 3; and (c) an air distribution mechanism 5, 6, and/or 7.

The air distribution mechanism may be a fan 5 or any other suitable mechanism for moving fluid, e.g., air, through the diffuser apparatus. In accordance with certain aspects of the invention, the selection, design, sizing, and operation of the air distribution mechanism should be such that the fluid, e.g. air, flow through the diffuser apparatus is generally as rapid as is practical. Without intending to be limited by theory, it is believed that optimal levels of PHPG are generated for exiting the diffuser apparatus under rapid fluid flow conditions.

The ultraviolet light source 4 may generally produce at least one range of wavelengths sufficient to activate photocatalytic reactions of the humid ambient air, but without photolyzing oxygen so as to initiate the formation of ozone. In one embodiment, the ultraviolet light produces at least one wavelength in a range above about 181 nm, above about 185 nm, above about 187 nm, between about 182 nm and about 254 nm, between about 187 nm and about 250 nm, between about 188 nm and about 249 nm, etc. Such wavelengths will generally produce PHPG including hydrogen peroxide in the substantial absence of ozone.

In accordance with the present invention, the term "substantial absence of ozone" generally means amounts of ozone below about 0.015 ppm, down to levels below the LOD (level of detection) for ozone. Such levels are below the generally accepted limits for human health. In this regard, the Food and Drug Administration (FDA) requires ozone output of indoor medical devices to be no more than 0.05 ppm of ozone. The Occupational Safety and Health Administration (OSHA) requires that workers not be exposed to an average concentration of more than 0.10 ppm of ozone for 8 hours. The National Institute of Occupational Safety and Health (NIOSH) recommends an upper limit of 0.10 ppm of ozone, not to be exceeded at any time. EPA's National Ambient Air Quality Standard for ozone is a maximum 8 hour average outdoor concentration of 0.08 ppm.

In certain embodiments the PHPG may, however, be used for the removal of ozone from the ambient environment by means of the following reaction:

$$O_3 + H_2O_2 \rightarrow H_2O + 2O_2$$

In certain embodiments the PHPG may be used for the removal of VOC's from the ambient environment by means of direct oxidation of VOC's by the PHPG.

In certain embodiments, the PHPG may be used for microbial control, including but not limited to, as a biocide, for indoor air treatment, as a mold and/or fungus eliminator, as a bacteria eliminator, and/or as an eliminator of viruses. The PHPG method may produce hydrogen peroxide gas sufficient to carry out a desired microbial control and/or disinfection/remediation process. A sufficient amount is generally known by those skilled in the art and may vary depending on the solid, liquid, or gas to be purified and the nature of a particular disinfection/remediation.

In certain embodiments, with reference to the microbial control and/or disinfection/remediation of air and related environments (including surfaces therein), the amount of PHPG may vary from about 0.005 ppm to about 0.10 ppm, more particularly, from about 0.02 ppm to about 0.05 ppm, in the environment to be disinfected. Such amounts have been proven effective against, e.g., the *Feline Calicivirus* (an EPA approved surrogate for Norovirus), Methicillin Resistant *Staphylococcus Aureus* (MRSA), Vancomyacin Resistant *Enterococcus Faecalis* (VRE), *Clostridium Difficile* (C-Diff), *Geobacillus Stearothermophilus*, and *Aspergillus Niger*. Such amounts of PHPG are safe to use in occupied areas (including, but not limited to, schools, hospitals, offices, homes, and other common areas), disinfect surface contaminating microbes, kill airborne pathogens, and provide microbial control, e.g., for preventing the spread of Pandemic Flu, controlling nosocomial infections, and reducing the transmission of common illnesses.

In certain aspects of the invention, the humidity of the ambient air is preferably above about 1% relative humidity (RH), above about 5% RH, above about 10% RH, etc. In certain embodiments, the humidity of the ambient air may be between about 10% and about 99% RH. In one embodiment, the method of the invention includes regulating the humidity of the ambient air within the range of about 5% to about 99% RH, or about 10 to about 99% RH.

The metal, or metal oxide, catalyst may be selected from titanium dioxide, copper, copper oxide, zinc, zinc oxide, iron, and iron oxide or mixtures thereof, and more preferably, the catalyst is titanium dioxide. More particularly, titanium dioxide is a semiconductor, absorbing light in the near ultraviolet portion of the electromagnetic spectrum. Titanium dioxide is synthesized in two forms—anatase and rutile—which are, in actuality, different planes of the same parent crystal structure. The form taken is a function of the preparation method and the starting material used. Anatase absorbs photons at wavelengths less than 380 nm, whereas rutile absorbs photons at wavelengths less than 405 nm.

A layer of titanium dioxide approximately 4 μm thick will absorb 100% of incident low wavelength light. Titanium dioxide is known to have approximately $9-14 \times 10^{14}$ active surface sites per square centimeter. An active surface site is a coordinatively unsaturated site on the surface which is capable of bonding with hydroxyl ions or other basic species. Its photocatalytic activity is influenced by its structure (anatase or rutile), surface area, size distribution, porosity, and the density of hydroxyl groups on its surface. Anatase is generally considered to a more active photocatalyst than rutile. It is known to adsorb dioxygen more strongly than rutile and remains photoconductive longer after flash irradiation than rutile. Anatase and rutile have band gap energies of 3.2 and 3.0 electron volts (eV), respectively.

Numerous agents have been shown to have an influence on photocatalysis. Such agents may be added to the reaction environment to influence the photocatalysis process. As recognized by those skilled in the art, some agents enhance the process, while others degrade it. Still others act to enhance one reaction while inhibiting another.

From acid-base chemistry, it has been found that basic agents may bond at the active site on the catalyst. Without being limited by theory, reducible agents which adsorb on the catalyst more strongly than dioxygen may substitute as the electron acceptor. Small molecule chemicals, metals, and ions have all shown this capability. In these cases, the impact on formation of PHPG are dictated by the efficiency with which the agent accepts electrons relative to dioxygen and hydrogen peroxide.

Some additive agents involve radical species in side reactions or in the formation of less reactive radicals incapable of performing the desired reaction. Yet others physically alter the photocatalyst, changing its performance. In accordance with the present invention, additive agents may be selected to optimize the formation of PHPG (optionally while minimizing or eliminating the formation of ozone, plasma species, or organic species).

In one aspect, as mentioned above, additive agents may include co-catalysts. Co-catalysts may be metals or coatings deposited on the surface of a catalyst to improve the efficiency of selected PHPG reactions. Cocatalysts may alter the physical characteristics of catalyst in two ways. First, they may provide new energy levels for conduction band electrons to occupy. Second, co-catalysts may possess different absorption characteristics than the supporting photocatalyst. This may cause the order in which competing reactions take place on the co-catalyst to be different from that on the catalyst itself. Cocatalysts are generally most effective at surface coverages of less than five percent.

Typical co-catalysts may be selected from platinum, silver, nickel, palladium, and many other metal compounds. Phthalocyanine has also demonstrated cocatalytic capabilities.

A diffuser apparatus in accordance with the invention may be of any suitable shape or size, including spherical, hemispherical, cubic, three dimensional rectangular, etc. Diffusers may also be configured in any number of fanciful shapes such as teddy bears, piggy banks, mock radio's, etc. The core of the diffuser apparatus may be comprised of an ultraviolet light source. The ultraviolet light source 4 may be positioned at the center, or interior, of the diffuser apparatus, may be of varied intensity depending on the size of the apparatus and the application for which it is intended. By way of example, In certain embodiments, with reference to FIG. 1, the ultraviolet source 4, e.g., may be tubular in shape may be contained within an elongated wedge-shaped, or tube shaped diffuser shell 2. In certain configurations a reflector 1 may serve to focus light in a specific direction within the interior of a device as required by its specific shape.

The shell 2 of the diffuser apparatus may be formed from any suitable substrate material, including ceramic, porcelain, polymer, etc. By way of example, the polymer may be a porous or vented polymer that is both hydrophobic and resistant to degradation by ultraviolet light in the 254 nm to 182 nm range. Polymers that are resistant to some wavelengths within this range, but not all, may be used in conjunction with UV lamps that only produce light in the ranges to which they are resistant. A diffuser shell may be molded into any desired size and shape, and formed as any color desired. In certain embodiments, a phosphorescent material may be incorporated into the shell material so as to emit visible light upon absorption of UV light.

In one embodiment, the interior surface of the diffuser shell may generally be used as the substrate by coating it with photocatalyst, which may include titanium dioxide doped with one or more other metals in certain embodiments. By way of example, the photocatalyst may be applied to the interior of the diffuser substrate as a paint. The application should generally be applied so as to prevent clogging of the pores within the diffuser substrate. In one embodiment, air may be applied to the substrate, and forced through the pores of the substrate after application of the photocatalyst paint, both causing the coating to dry and keeping the pores clear by means of forced air. It may be preferred for the combination of photocatalytic coating and diffuser substrate to be opaque enough to prevent UV light from escaping the assembled diffuser apparatus.

In another embodiment, the diffuser shell and the catalyst substrate are separate components, with the substrate layer situated just inside, and very close to, the interior surface of the diffuser shell.

The diffuser design optimizes PHPG production by spreading the air permeable photocatalytic reactor surface thinly over a large area that is perpendicular to air flow, rather than by compacting it into a volume-optimizing morphology designed to maximize residence time within the reactor. By configuring the reactor morphology as a thin, sail-like air-permeable structure, just inside the diffuser's interior shell, the exit path length for hydrogen peroxide molecules produced on the catalyst becomes very short, and their residence time within the reactor structure is reduced to a fraction of a second, preventing the vast majority of hydrogen peroxide molecules from being subsequently adsorbed onto the catalyst and reduced back into water. Also, by placing the catalyst substrate just inside the interior surface of the diffuser shell, not only is reactor surface area maximized, but the PHPG produced also passes out of the diffuser almost immediately and thus avoids photolysis from prolonged exposure to the UV light source. By means of this morphology, PHPG output concentrations as high as 0.08 ppm have been achieved.

In preferred embodiments, PHPG concentrations maybe self-regulating due to the electrostatic attraction between PHPG molecules, which degrade to water and oxygen upon reacting with each other. PHPG self-regulation occurs whenever the concentration of PHPG results in intermolecular spacing that is closer in distance than the electrostatic attraction range of the PHPG molecules. When this occurs, PHPG molecules are attracted to, and degrade each other until the concentration drops sufficiently that the intermolecular spacing is greater than the electrostatic attraction range of the PHPG molecules. By this means PHPG concentrations are maintained at levels well below the OSHA workplace safety limit of 1.0 parts per million.

It should be noted that this PHPG optimizing morphology also minimizes the residence time for any organic contaminants that may enter and pass through the system, dramatically reducing the probability that they will be oxidized. Effectively, photocatalytic systems optimized for PHPG production, are, by design, less likely to oxidize organic contaminants as they pass through the catalyst structure; and photocatalytic systems optimized for the oxidation of organic contaminants will, by design, inhibit hydrogen peroxide gas production.

The diffuser apparatus also generally includes a fluid distribution mechanism. The fluid distribution mechanism generally serves to move fluid, such as air through the diffuser apparatus. More particularly, the air distribution mechanism will generally direct fluid into the diffuser apparatus, which will then diffuse out through the diffuser substrate. In one embodiment, with reference to FIG. 2, the fluid distribution mechanism will direct fluid through an intake vent 7 to a small fan (not shown) framed within an opening 5 in the diffuser apparatus. The fan may also have a replaceable hydrophobic gas and/or dust filter 6 on the upstream side to prevent organic gases and/or dust from entering the diffuser apparatus, thus ensuring that the PHPG remains substantially free of organic species. Based on need, in certain embodiments, it may be desirable for the fluid distribution mechanism to be of the lowest power necessary to create a gentle overpressure within the diffuser; in other embodiments, a rapid fan speed may be more desirable.

In accordance with certain aspects of the invention, PHPG may be produced in the substantial absence of ozone, plasma species, and/or organic species, e.g., by the photocatalytic oxidation of adsorbed water molecules when activated with UV light in the ranges described herein. In one embodiment, the diffuser substrate, coated with photocatalyst on its interior (or diffuser shell lined on the interior with a thin sail-like air-permeable photocatalyst structure), may be placed over and around the ultraviolet lamp. An opening in the diffuser may serve as a frame into which the UV light's power source and structural support will fit. When assembled, the diffuser apparatus may function as follows: (a) the fluid distribution mechanism directs air into the diffuser through an organic vapor and dust filter, creating an overpressure; (b) air moves out of the diffuser through the pores or vents in the substrate and/or diffuser shell; (c) moisture contained in the air adsorbs onto the photocatalyst; (d) when illuminated, the UV light produced by the lamp activates the photocatalyst, causing it to oxidize adsorbed water and reduce adsorbed oxygen, producing PHPG; and (e) the PHPG produced in the interior of the diffuser apparatus then moves rapidly out of the diffuser through its pores or vents into the surrounding environment.

In some embodiments, PHPG may be generated by a Medium Pressure Mercury Arc (MPMA) Lamp. MPMA lamps emit not only ultraviolet light, but also visible light, and wavelengths in the infrared spectrum. It is important that when selecting a lamp, output in the ultraviolet spectrum should be closely examined. The ultraviolet spectral output is sometimes expressed graphically, showing the proportional output at the important ultraviolet wavelengths. The broad spectrum of the MPMA lamp is selected for its functionality.

In other embodiments, PHPG may be generated by Ultraviolet Light Emitting Diodes (UV LED's). UV LED's are more compact and banks of UV LED's can be arrayed in a variety of sizes and ways, enabling the production of smaller, more rugged systems.

In other embodiments, PHPG output may be regulated by control systems managing devices singly, or in groups. Such control systems may regulate operation by: (a) turning devices on and off; (b) regulating light intensity and/or fan speed; (c) monitoring ambient PHPG levels directly by means of automated colorimetric devices, by automated Draeger indicators, by means of flash vaporization of PHPG accumulated in an aqueous trap, by measuring the change in conductivity of a substrate sensitive to hydrogen peroxide accumulation, or by thermal means, measuring the heat evolved by the exothermic reaction between PHPG and a stable reactant to which it is electrostatically attracted; and (d) monitoring ambient PHPG levels indirectly through relative humidity.

EXAMPLES

Without intent to be limited by the following performance example, one embodiment of the invention was constructed as follows: (a) the device was constructed in the shape of a quarter-cylinder 20 inches in length, and with a radius of 8.5 inches; (b) the quarter cylinder was designed to fit into the 90 degree angle formed where a wall meets a ceiling, with the quarter-cylinder's straight sides fitting flush against the wall and ceiling, and the curved face of the cylinder facing out and down into the room; (c) as viewed from below, the right end of the quarter-cylinder supported a variable speed fan with a maximum output of 240 cubic feet per minute, and a high efficiency, hydrophobic, activated charcoal intake filter; (d) the left end of the quarter cylinder supported the power connection for the fan, and a fourteen inch Medium Pressure Mercury Arc (MPMA) lamp, positioned so that the lamp was centered within, and parallel to, the length of the quarter-cylinder; (e) a vented metal reflector was placed behind the MPMA lamp to reflect light toward the interior surface of the curved face of the quarter-cylinder; and (f) the curved face of the cylinder was vented to allow air, but not light, to flow out of the device.

A curved sail-like photocatalyst structure was placed just inside, and parallel to, the interior surface of the curved face of the quarter-cylinder; (a) the catalyst substrate was eighteen inches long, eleven inches high, framed, and had a curvature from top to bottom with a radius of 8.25 inches; (b) was formed of fiberglass, and was coated with crystalline titanium dioxide powder; and (c) the titanium dioxide was applied to the fiberglass in five coats to ensure complete coverage of all fibers, then sintered in an oven to cause the photocatalyst crystals to bond both to each other and to the fiberglass.

During operation, both the fan and the MPMA lamp were turned on: (a) intake air was drawn into the device through the high efficiency, hydrophobic, activated charcoal intake filter which removed by adsorption Volatile Organic hydroCarbons (VOC's), without removing moisture from the intake air; (b) the intake air was supplied to the back of the device, where the vented metal reflector redirected it evenly toward the photocatalyst structure, and the interior of the vented face of the quarter-cylinder; (c) moisture and oxygen from the intake air adsorbed onto the photocatalyst, which was activated by 254 nm light from the MPMA lamp; (d) the activated photocatalyst oxidized water to hydroxyl radicals, which then combined to form hydrogen peroxide, while dioxygen was simultaneously reduced on the photocatalyst to hydrogen peroxide; and (e) the Purified Hydrogen Peroxide Gas (PHPG) generated was immediately carried by the air flow off of the photocatalyst, through the light-impermeable vented face of the device, and out into the room.

The Purified Hydrogen Peroxide Gas (PHPG) thus produced was: (a) substantially free of bonded water because it was produced by catalytic means rather than by the vaporization of aqueous solution; (b) the PHPG was substantially free of ozone because the MPMA lamp did not use any wavelengths capable of photolyzing dioxygen; (c) the PHPG was substantially free of plasma species because the morphology of the photocatalyst permitted the rapid removal of hydrogen peroxide from its surface before it could subsequently be reduced photocatalytically; (d) the PHPG was protected from Ultraviolet (UV) photolysis because it passed out through the light-impermeable, vented face of the quarter-cylinder immediately upon exiting the photocatalyst surface; and (e) the PHPG was substantially free of organic species because VOC's were adsorbed by the high efficiency, hydrophobic, activated charcoal intake filter.

The device was subjected to tests designed and implemented by two accredited laboratories to: (a) measure the output of Purified Hydrogen Peroxide Gas (PHPG); (b) confirm that the output was substantially free of ozone; (c) confirm that the output was substantially free of VOC's; (d) measure the efficacy of PHPG against the *Feline Calicivirus* (an EPA-approved substitute for noroviruses), Methicillin Resistant *Staphylococcus aureus* (MRSA), Vancomycin Resistant *Enterococcus faecalis* (VRE), *Clostridium difficile* (C-Diff), *Geobacillus stearothermophilus*, (a stable bacteria used by the insurance industry to verify successful microbial remediation), and *Aspergillus niger* (a common fungus); and (e) test at a variety of ambient relative humidity's including 35% to 40% at 70 to 72 degrees Fahrenheit, 56% to 59% at 81 to 85 degrees Fahrenheit, and 98% at 78 degrees Fahrenheit.

Measurements for ozone, VOC's, temperature, and humidity were all accomplished using standard devices. Since no device is yet readily available to measure hydrogen peroxide gas at levels below 0.10 ppm, three new means were devised: (a) hydrogen peroxide test strips, normally used to measure approximate concentrations in aqueous solution, were found to detect the presence of PHPG over time; (b) hydrogen peroxide test strips, normally designed to be read after 20 seconds of exposure, were found to accumulate PHPG, and to provide approximate readings of PHPG concentration accurate to within 0.01 ppm, when normalized for exposure time over periods of less than an hour—for example, a test strip that accumulated 0.5 ppm over the course of five minutes was exposed for 15 twenty-second intervals, indicating an approximate concentration of 0.5 ppm divided by 15, or 0.033 ppm; (c) Draeger tubes, designed to detect hydrogen peroxide concentrations as low as 0.10 ppm after drawing 2000 cubic centimeters of air, were found to provide readings of lower concentrations accurate within 0.005 ppm, as larger volumes were drawn by a calibrated pump—for example, a Draeger tube that indicated 0.10 ppm after drawing 4000 cubic centimeters measured an approximate PHPG concentration of 0.05 ppm, and a Draeger tube that indicated 0.10 ppm after drawing 6000 cubic centimeters, measured an approximate PHPG concentration of 0.033 ppm; and (d) measurements taken with both hydrogen peroxide test strips and Draeger tubes were found to closely agree with each other.

In tests designed to measure hydrogen peroxide levels at varying humidities, the following data was collected:

| Relative Humidity | Temperature (Fahrenheit) | PHPG Concentration | Means of Detection/Measurement |
|---|---|---|---|
| 98% | 78 | 0.08 ppm | Test strip/Draeger tube/ Microbial reduction |
| 56%-59% | 81-85 | 0.05-0.08 ppm | Test strip/Draeger tube/ Microbial reduction |
| 35%-40% | 70-72 | 0.005-0.01 ppm | Test strip/ Microbial reduction |

The PHPG measurement data indicated that the concentration of PHPG produced is highly dependent on the relative humidity. This is predictable, because the production of PHPG is directly dependent on the availability of water molecules in the air. It should be noted that the US Department of Health and Human Services requires that hospital operating rooms be maintained between 30% and 60% relative humidity.

The PHPG measurement data also remained constant over time and indicated an upper equilibrium limit of approximately 0.08 ppm. This is also predictable due to the electrostatic attraction of PHPG molecules to each other whenever their intermolecular spacing becomes less than their mutual electrostatic attraction ranges. Under this condition excess PHPG reacts with itself to produce oxygen and water molecules. This upper limit of 0.08 ppm is also well below the OSHA workplace safety limit of 1.0 ppm and thus safe to breathe, indicating that PHPG systems can be safely and continuously used in occupied areas.

All testing also indicated a complete absence of ozone in the device's output.

In VOC testing, an approximate ambient concentration of 7 ppm of 2-propanol was established 2500 cubic foot room.

The device was found to rapidly reduce VOC levels throughout the room.

| | VOC (ppm) | | | | | $H_2O_2$ (ppm)-Draeger | Ozone ppm |
|---|---|---|---|---|---|---|---|
| Station: | 1 | 2 | 3 | 4 | 5 | | |
| Distance | 2" | 9' | 12' | 16' | 20' | | |
| Zero Time | 6.8 | 7.0 | 6.8 | 6.8 | 6.7 | | |
| Unit's Light and fan (high) turned on | | | | | | | |
| 5 min | 6.0 | 5.7 | 5.6 | 5.6 | 5.6 | | |
| 10 min | 4.2 | 4.4 | 3.7 | 3.9 | 3.6 | | |
| 15 min | 3.6 | 3.6 | 3.1 | 3.1 | 2.9 | | |
| 30 min | 1.2 | 1.3 | 1.1 | 1.1 | 1.1 | | |
| 60 min | 0.4 | 0.6 | 0.9 | 0.4 | 0.2 | 0.05 at room center | |
| 90 min | 0.1 | 0.4 | 0.5 | 0.3 | 0.2 | | 0.000 all St |
| 24 hr | 0.0 | 0.0 | 0.0 | 0.0 | 0.0 | 0.08 at center & S-5 | 0.000 all St |

In qualitative microbial testing, chips inoculated with *Geobacillus Stearothermophilus* were placed in the environment in several tests, and in all cases showed significant reduction of the bacteria within a matter of hours.

In quantitative microbial testing at ATS labs in Eagan, Minn. the following data was collected. It should be noted that these impressive kill rates were achieved with a PHPG concentration of just 0.005 ppm to 0.01 ppm, produced at a relative humidity of 35% to 40%.

| Test Organism | Exposure Time (hrs) | Average Virus Infectivity Observed After Exposure | Percent Reduction as Compared to Time Zero Virus Control | Percent Reduction Compared to Corresponding Natural Die-off |
|---|---|---|---|---|
| Feline Calicivirus (Norovirus substitute) | 2 | 4.3 $\log_{10}$ | 99.5% | 96.8% |
| | 6 | 2.3 $\log_{10}$ | 99.995% | 99.8% |
| | 24 | ≤0.6 $\log_{10}$ (virus detected in only one replicate) | ≥99.9999% | 99.8% |

| Test Organism | Time point | Average CFU/Test carrier (Survivors in the test) | Percent Reduction as Compared to Time Zero Control | Percent Reduction Compared to Corresponding Natural Die-off |
|---|---|---|---|---|
| MRSA (ATCC 33592) | 2 hours | <1 (no survivors) | >99.9999% | >99.9999% |
| | 6 hours | <1 (no survivors) | >99.9999% | >99.9999% |
| | 24 hours | <1 (no survivors) | >99.9999% | >99.9999% |
| VRE (ATCC 51575) | 2 hours | <1 (no survivors) | >99.9999% | >99.999% |
| | 6 hours | <1 (no survivors) | >99.9999% | >99.99% |
| | 24 hours | <1 (no survivors) | >99.9999% | >99.9% |
| C. difficile (ATCC 700792) | 2 hours | $2.18 \times 10^5$ CFU/Carrier | 27.3% | 9.2% |
| | 6 hours | $1.1 \times 10^5$ CFU/Carrier | 63.3% | 60.6% |
| | 24 hours | $7.3 \times 10^4$ CFU/Carrier | 75.7% | 70.4% |
| A. niger (ATCC 16404) | 2 hours | $1.9 \times 10^5$ CFU/Carrier | 19.1% | 13.6% |
| | 6 hours | $4.67 \times 10^4$ CFU/Carrier | 80.1% | 81.3% |
| | 24 hours | $1.2 \times 10^4$ CFU/Carrier | 94.9% | 90.8% |

At higher humidities, higher concentrations of PHPG are produced, and microbial reduction rates will increase. The data collected above at 56% to 59% relative humidity indicates that a PHPG concentration at least eight times higher than used in this quantitative test can be achieved.

Also, a comparison test indicated that the PHPG test device produces a PHPG equilibrium concentration up to 150 times greater than the incidental output of unpurified hydrogen peroxide from a standard photocatalytic cell.

Generally, the invention has been described in specific embodiments with some degree of particularity, it is to be understood that this description has been given only by way of example and that numerous changes in the details of construction, fabrication and use, including the combination and arrangement of parts, may be made without departing from the spirit and scope of the invention.

What is claimed:

1. A method for remediation of an environment comprising:
   (a) generating a gas comprising non-hydrated hydrogen peroxide gas, wherein said non-hydrated hydrogen peroxide gas comprises 0.015 ppm of ozone or less and that is free of plasma species, and organic species
   (b) directing said non-hydrated hydrogen peroxide gas into said environment;
   (c) maintaining said non-hydrated hydrogen peroxide gas in said environment at a concentration between 0.005 ppm to 0.10 ppm;
   wherein said remediation is the elimination of mold or fungus.

2. The method of claim 1, wherein said non-hydrated hydrogen peroxide gas interacts directly with said environment electrostatically.

3. The method of claim 1, wherein said environment is selected from the group consisting of a school, a hospital, an office, and a home.

4. The method of claim 1, further comprising the disinfection of said environment of bacteria and viruses.

5. The method of claim 1, wherein said gas comprising non-hydrated hydrogen peroxide gas is generated from air by exposing a metal, or metal oxide, catalyst to ultraviolet light in the presence of said air for a residence time on said catalyst of less than a second, and said air comprises a percent humidity within the range of 5-99%.

6. The method of claim 5, wherein said air is ambient humid air.

7. The method of claim 5, wherein said metal or metal oxide catalyst is titanium dioxide.

8. The method of claim 6, further comprising allowing said non-hydrated hydrogen peroxide gas to remove both ozone and volatile organic compounds (VOC's) from the ambient air by means of direct chemical reaction of these species with said non-hydrated hydrogen peroxide gas, said removal via, at least (a) reacting with said ozone to produce oxygen and water, and (b) reacting with said VOC's to produce carbon dioxide and water.

9. The method of claim 5, further comprising regulating said air within the range of about 5% to about 99% relative humidity.

10. The method of claim 1, wherein said environment is an occupied area.

11. A method for disinfecting an environment comprising:
    (a) generating a gas comprising non-hydrated hydrogen peroxide gas, wherein said non-hydrated hydrogen peroxide gas comprises 0.015 ppm of ozone or less and that is free of plasma species, and organic species
    (b) directing said non-hydrated hydrogen peroxide gas into said environment;
    (c) maintaining said non-hydrated hydrogen peroxide gas in said environment at a concentration between 0.005 ppm to 0.10 ppm;

wherein said disinfecting is a reduction of virus infectivity or a reduction in the average number of colony forming units of a bacteria.

12. The method of claim 11, wherein said virus infectivity is reduced by 99% or more within two hours.

13. The method of claim 11, wherein said average number of colony forming units of a bacteria is reduced by an amount selected from the group consisting of 9.2% or more within two hours, 99% or more within two hours, 60.6% or more within 6 hours, 81.3% or more within 6 hours, greater than 99.99% within 6 hours, 70.4% or more within 24 hours, 90.8% or more within 24 hours, and greater than 99.9% within 24 hours, and greater than 99.99% within 24 hours.

14. The method of claim 11, wherein said environment is selected from the group consisting of a school, a hospital, an office, and a home.

15. The method of claim 14, wherein said environment is a hospital.

16. The method of claim 15, wherein said bacteria is selected from the group consisting of Methicillin Resistant *Staphylococcus aureus* (MRSA), Vancomycin Resistant *Enterococcus faecalis* (VRE), *Clostridium difficile* (C-Diff), and *Geobacillus stearothermophilus*.

17. The method of claim 11, wherein said gas comprising non-hydrated hydrogen peroxide gas is generated from air by exposing a metal, or metal oxide, catalyst to ultraviolet light in the presence of said air for a residence time on said catalyst of less than a second, and said air comprises a percent humidity within the range of 5-99%.

18. The method of claim 17, wherein said air is ambient humid air.

19. The method of claim 17, wherein said metal or metal oxide catalyst is titanium dioxide.

20. The method of claim 17, further comprising regulating said air within the range of about 5% to about 99% relative humidity.

21. The method of claim 11, wherein said environment is an occupied area.

22. The method of claim 11, further comprising allowing said non-hydrated hydrogen peroxide gas to remove both ozone and volatile organic compounds (VOC's) from the ambient air by means of direct chemical reaction of these species with said non-hydrated hydrogen peroxide gas, said removal via, at least (a) reacting with said ozone to produce oxygen and water, and (b) reacting with said VOC's to produce carbon dioxide and water.

* * * * *